United States Patent
Tanaka

(10) Patent No.: US 6,319,705 B1
(45) Date of Patent: Nov. 20, 2001

(54) MICROCHIP DEVICE FOR ELECTROPHORESIS

(75) Inventor: Hiroshi Tanaka, Kyoto (JP)

(73) Assignee: Shimadzu Corporation (JP)

( * ) Notice: Subject to any disclaimer, the term of this patent is extended or adjusted under 35 U.S.C. 154(b) by 0 days.

(21) Appl. No.: 09/498,160

(22) Filed: Feb. 4, 2000

(30) Foreign Application Priority Data

Mar. 31, 1999 (JP) .................................................. 11-090852

(51) Int. Cl.$^7$ .............................. C12M 1/34; C12M 3/00
(52) U.S. Cl. ...................... 435/287.1; 204/450; 204/451; 204/556; 204/600; 204/601; 204/603; 204/194; 204/400; 422/68.1; 422/70; 422/82.05; 422/55; 422/58; 422/61; 422/62; 422/63; 422/82.08; 422/82.09; 422/98; 422/103; 422/110; 435/287.3; 435/288.2; 435/288.5; 435/288.7; 436/514; 436/805; 436/806; 436/807; 436/809; 436/824
(58) Field of Search ..................................... 204/450, 451, 204/556, 600, 601, 603, 194, 400; 422/68.1, 70, 82.05, 55, 58, 61, 62, 63, 82.08, 82.09, 98, 103, 110; 435/287.1, 287.3, 288.2

(56) References Cited

U.S. PATENT DOCUMENTS

| | | | |
|---|---|---|---|
| 5,180,480 | * | 1/1993 | Manz ..................... 204/299 |
| 5,323,010 | * | 6/1994 | Gratton et al. ................... 250/458.1 |
| 5,599,432 | * | 2/1997 | Manz et al. ........................ 204/451 |
| 5,627,643 | * | 5/1997 | Birnbaum et al. .................... 356/344 |
| 5,653,539 | * | 8/1997 | Rosengaus ........................... 374/159 |
| 5,858,195 | * | 1/1999 | Ramsey ............................... 204/601 |
| 5,880,071 | * | 3/1999 | Parce et al. .......................... 204/453 |
| 5,942,443 | * | 8/1999 | Parce et al. .......................... 436/514 |
| 6,174,675 | * | 1/2001 | Chow et al. .............................. 435/6 |

FOREIGN PATENT DOCUMENTS

| | | | | |
|---|---|---|---|---|
| 57-111422 | * | 7/1982 | (JP) | ................................. G01J/3/18 |
| WO-89/00280-A1 | * | 1/1989 | (WO) | .............................. G01J/3/28 |
| WO-95/32408-A1 | * | 11/1995 | (WO) | ............................... G01J/3/44 |

OTHER PUBLICATIONS

Harrison et al. (1993). Micromachining a miniaturized capillary electrophorisis–based chemical analysis system on a chip. Science. 261:895–897.*

Chiem et al. (1998). Monoclonal antibody binding affinity determined by microchip–based capillary electrophoresis. Electrophoresis. 19:3040–3044.*

Jacobson et al. (1995). Microchip electrophoresis with sample stacking. Electrophoresis. 16:481–486.*

* cited by examiner

Primary Examiner—Bao-Thuy L. Nguyen
(74) Attorney, Agent, or Firm—Coudert Brothers

(57) ABSTRACT

A microchip device for electrophoresis includes not only a microchip having a separation flow route for separating a sample electrophoretically and an electrical power source for applying a migration potential difference along the separation flow route but also a grating for dispersing light received from each position within a specified range along the separation flow route in a direction perpendicular to the separation flow route, a two-dimensional light-receiving device such as charge-coupled devices for receiving dispersed light from the grating at light-receiving positions which are two-dimensionally distributed parallel to and and perpendicular to the separation flow route, and a data processor for receiving measured values obtained repeatedly by said two-dimensional light-receiving means and carrying out multi-point averaging on the measured values for each of the light-receiving positions.

6 Claims, 4 Drawing Sheets

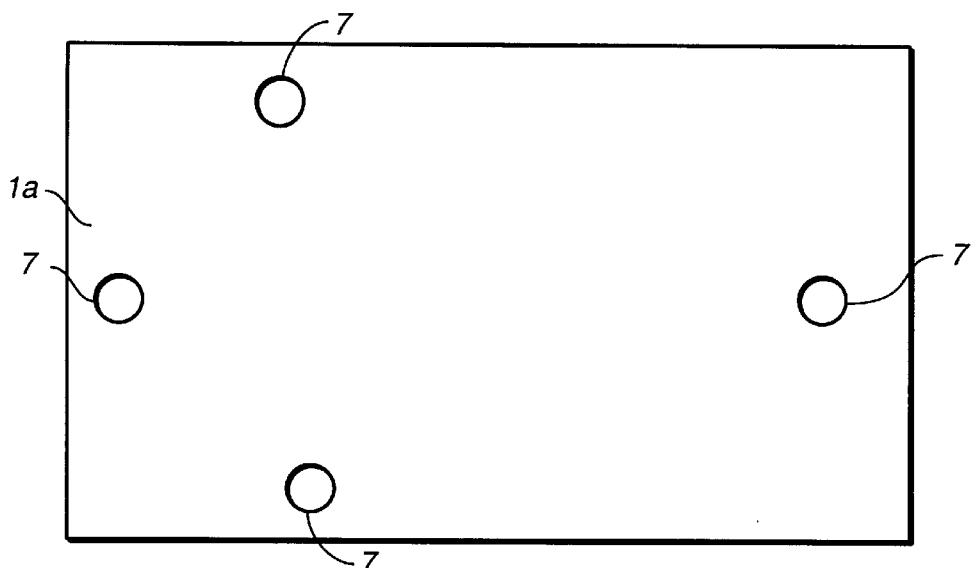
FIG._1A (PRIOR ART)
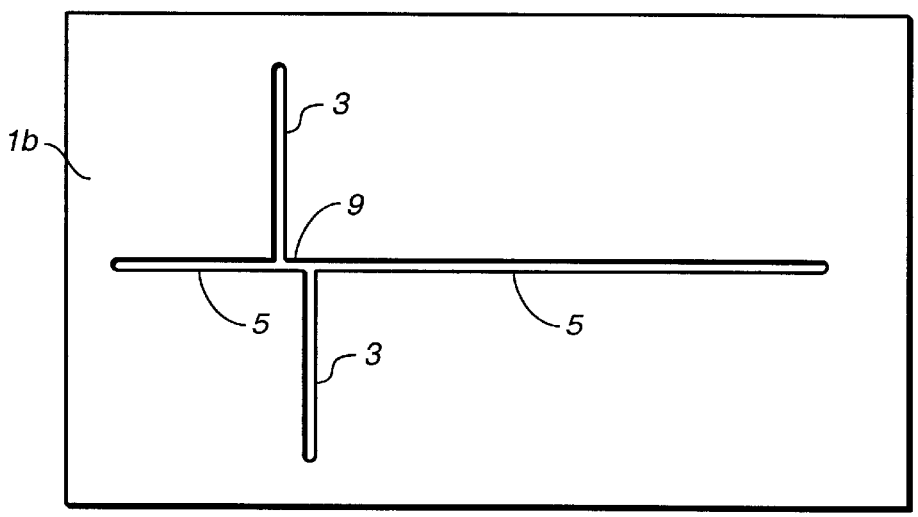
FIG._1B (PRIOR ART)
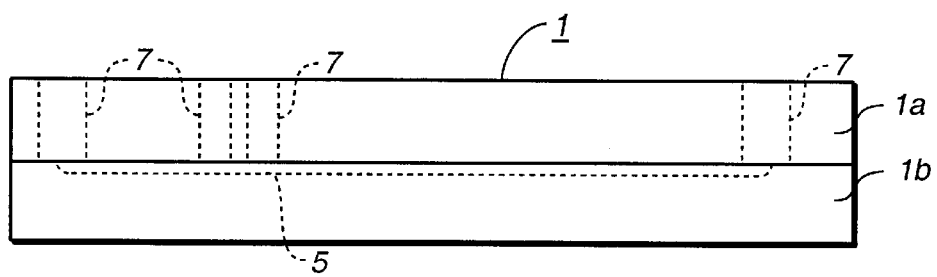
FIG._1C (PRIOR ART)

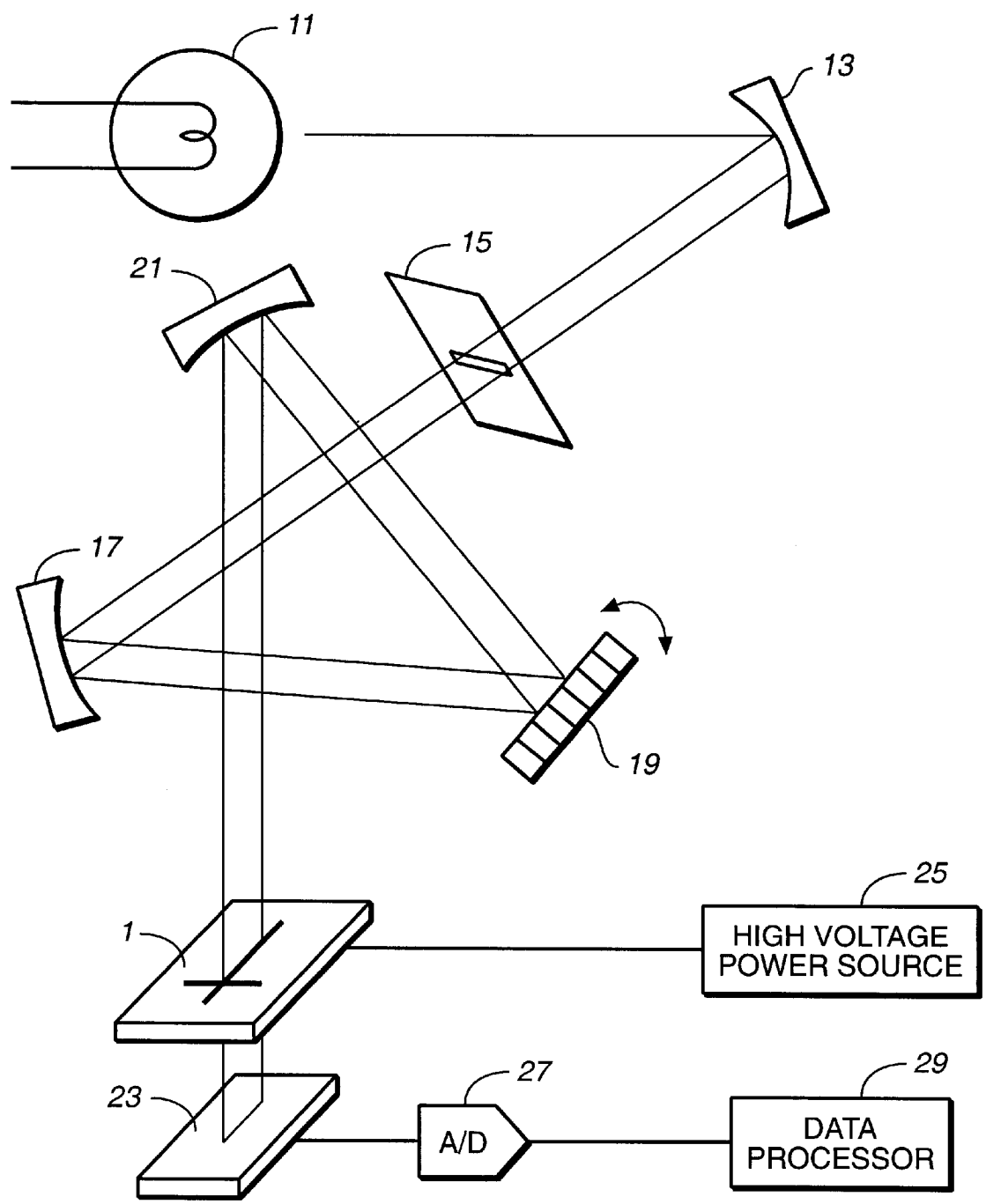
FIG._2 (PRIOR ART)

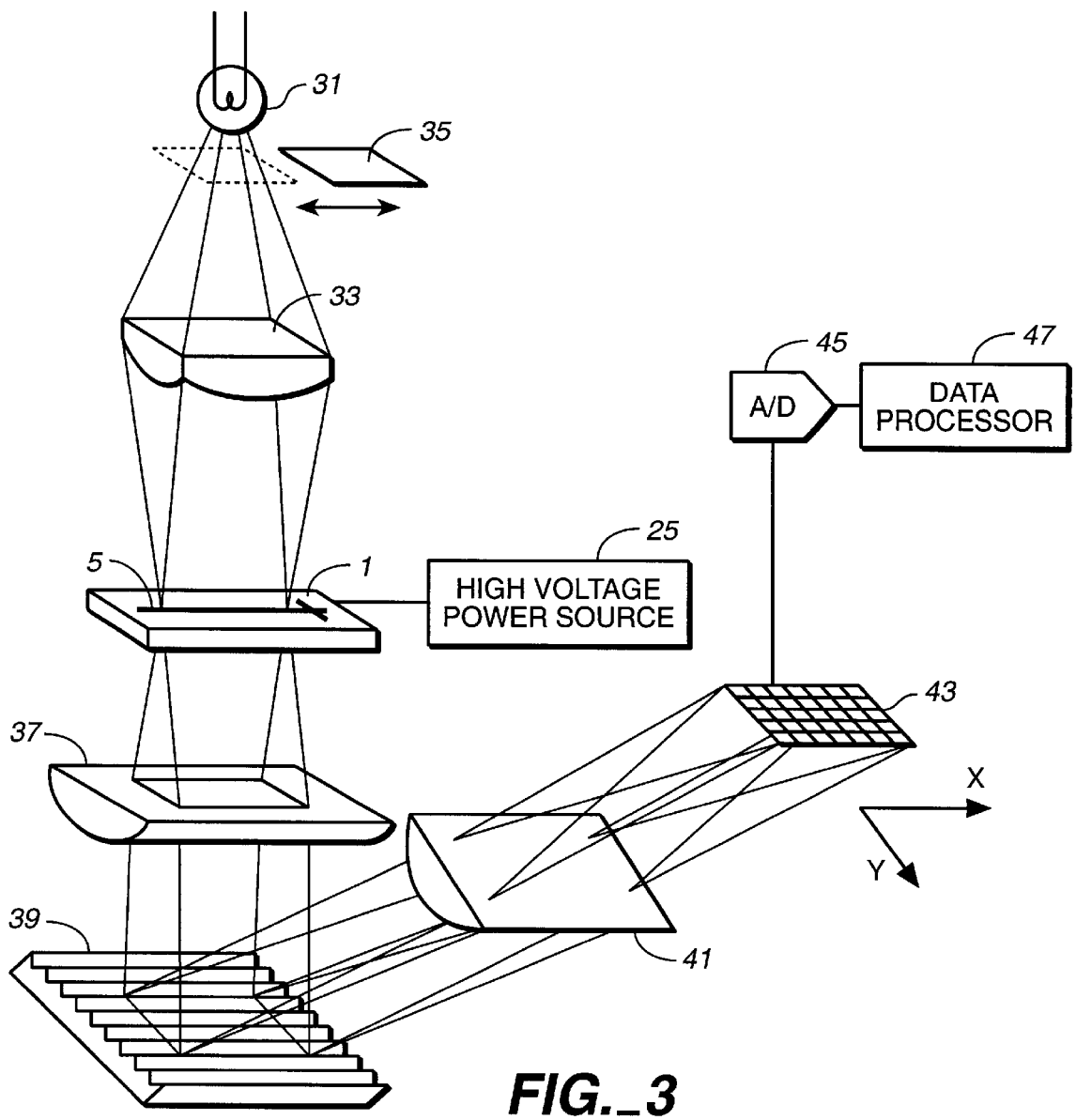
FIG._3

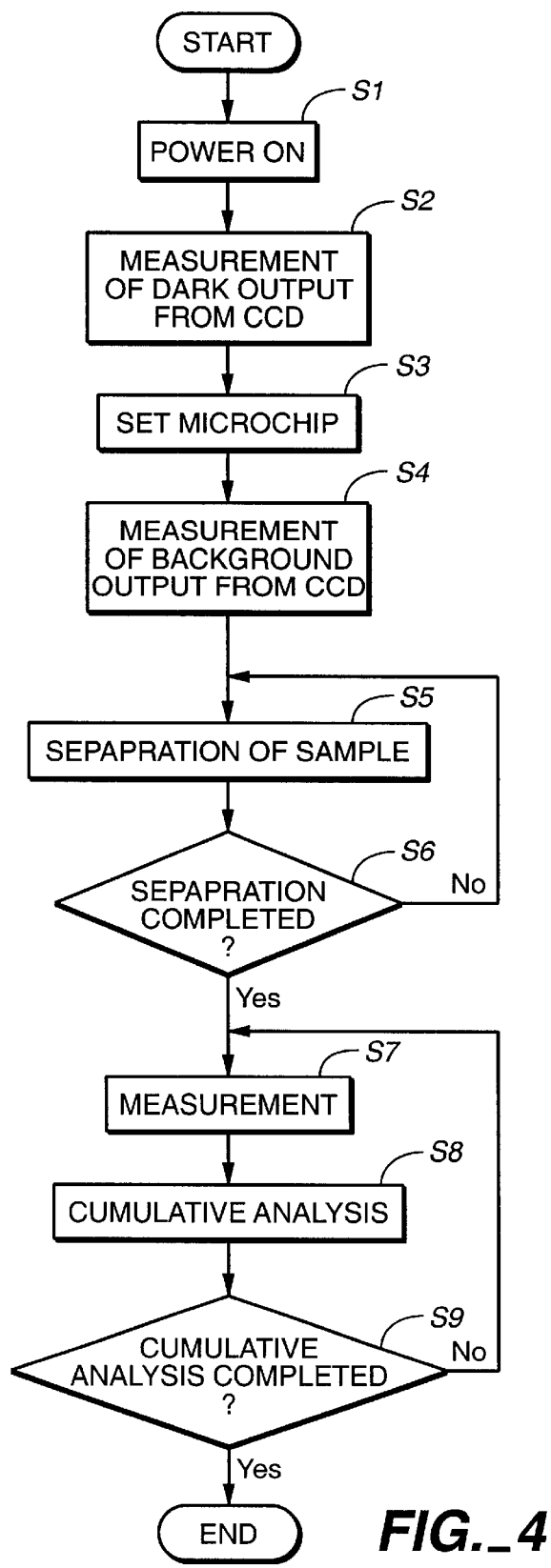
FIG._4

MICROCHIP DEVICE FOR ELECTROPHORESIS

BACKGROUND OF THE INVENTION

This invention relates to a device for electrophoresis capable of analyzing extremely small quantities of samples at a very high speed and with a high resolution. More particularly, the invention relates to a device for electrophoresis referred to as a "microchip" having a separation flow route formed inside transparent planar members and throughholes provided to one of the surfaces at positions corresponding to both ends of the separation flow route and reaching to this flow route.

Devices for electrophoresis have been in use for analyzing a very small quantity of protein or nucleic acid, and those using a capillary have been representative examples. Devices of this type have a glass capillary with internal diameter less than 100 $\mu$m and, after it is filled with a buffer and a sample is introduced at one of its ends, a high potential difference is applied between its ends and the target substance of analysis is dispersed inside the capillary. The application of a high potential is possible because the interior of the capillary has a relatively large surface area compared to its small volume and hence has a high cooling efficiency, and hence even a very small quantity of a sample such as DNA can be analyzed speedily and at a high resolution.

Since capillaries are easily breakable, having outer diameters as smaller as several 10–100 $\mu$m, it is not an easy job for the user to exchange them. In view of this problem capillary devices for electrophoresis comprising two base plates joined together (referred to as the microchip) have been proposed as a form of device for electrophoresis which can take the place of the capillaries of the conventional kind, being capable of carrying out an analysis speedily and allowing the device to be easily miniaturized, as shown, for example, by D. J. Harrison et al (Anal, Chem. Acta 283 (1993) 361–366).

FIGS. 1A, 1B and 1C show an example of such a microchip 1, characterized as comprising a pair of transparent base plates 1a and 1b (for example, of glass, quartz or a resin material), mutually intersecting capillary grooves 3 and 5 being formed on a surface of one of these base plates (1b) and the other base plate (1a) being provided with reservoirs 7 in the form of a throughhole at positions corresponding to the end points of these grooves 3 and 5.

When the microchip 1 thus structured is used for carrying out an analysis, the two base plates 1a and 1b are stacked one on top of the other as shown in FIG. 1C, and a migration liquid is injected into the grooves 3 and 5 from one of the reservoirs 7. After a sample is injected into one of the reservoirs 7 at one of the ends of the shorter groove 3 serving as the "sample introducing flow route", a high potential difference is applied between the reservoirs at both ends of this groove 3 such that the sample is dispersed throughout the groove 3.

Thereafter, a migration potential difference is applied between the reservoirs 7 at both ends of the longer groove 5 serving as the "separation flow route" such that the portion of the sample at the intersecting area 9 of the two grooves 3 and 5 begins to migrate inside the longer groove 5. If an optical detector is disposed at a suitable position on the longer groove 5, the separated portions of the sample transported through electrophoresis can be sequentially detected thereby.

A problem with such a microchip is that the detection sensitivity is relatively low because the optical path length inside the separation flow route is short. In view of this problem, there has been proposed a new kind of microchip device for electrophoresis, as shown in FIG. 2, adapted to stop the application of the migration potential when target components in the sample to be detected have been separated or while they are being separated, to expose the entire separation flow route to a light beam, to use a linear image sensor or the like to repeatedly measure the light absorption of fluorescence and to carry out a multi-point averaging process on the measured values at different positions along the separation flow route such that the detection sensitivity can be improved.

Explained more in detail with reference to FIG. 2, a first mirror 13, a slit 15 and a second mirror 17 are disposed along the optical path of the light from a light source 11 for obtaining a parallel beam of light from the source 11. The parallel beam of light thus prepared is passed through a dispersion grating 19. There is provided a third mirror 21 serving to lead only a selected portion of the light dispersed by the grating 19 having a specified wavelength to the microchip 1. Disposed on the opposite side of the microchip 1 away from the light-incident side is a photodiode array (PDA) 23 with a plurality of linearly aligned photodiodes for measuring the light from the separation flow route. A high-voltage electric power source 25 is connected to the microchip 1. The PDA 23 is provided with a data processor 29 adapted to receive signals from the individual photodiodes of the PDA 23 through an analog-to-digital (A/D) converter 27 and to carry out multi-point averaging of signals for each photodiode.

When a sample is to be analyzed with such a device, the sample is injected at one end of the sample introducing flow route 3 of the microchip 1 and potential differences are applied from the power source 25 between the ends of the flow routes 3 and 5 as explained above to firstly bring the sample to the intersection area 9 of the flow routes 3 and 5 and then to complete the separation of target components to be analyzed inside the separation flow route 5. Thereafter, the application of the potential difference is stopped and a beam of monochromatic light is made incident within a specified region along the separation flow route 5. At each of specified positions along the separation flow route 5, the distribution of mutual interaction between the separated components and the monochromatic light such as absorption or fluorescence is repeatedly measured by the PDA 23, and the signals from the PDA 23 are analyzed by a multi-point averaging routine by the date processor 29 for each of the photodiode to achieve a detection with high sensitivity.

The microchip device for electrophoresis shown in FIG. 2 may be characterized as irradiating a specified area along the separation flow route 5 with a monochromatic beam of light with a wavelength selected by the grating 19. If a spectrum over a certain range of wavelengths is desired, however, it is necessary to vary a parameter (such as the angle of orientation) of the grating 19 and to thereby sequentially measure the reaction between the monochromatic light of different wavelengths and separated components. If it is desired to maintain the same level of detection sensitivity over the given range of wavelengths, measurement must be repeated at different wavelengths but the time required for the measurements becomes inconveniently long. Not only is it impossible to conclude the analysis quickly, but if the time for the measurements is prolonged under a separated condition, the level of separation is also adversely affected due to the natural diffusion of the separated components.

SUMMARY OF THE INVENTION

It is therefore an object of this invention to provide a microchip device for electrophoresis with which a light spectrum from different positions along the separation flow route can be obtained quickly and with a high level of sensitivity.

A microchip device for electrophoresis embodying this invention, with which the above and other objects can be accomplished, may be characterized as comprising not only a microchip having a separation flow route formed between transparent planar members and throughholes which are formed through one of these transparent planar members at positions corresponding to end points of the separation flow route so as to reach the separation flow route and an electrical power source for applying a migration potential difference along the separation flow route but also a grating for dispersing light received from each position within a specified range along the separation flow route in a direction perpendicular to the separation flow route, a two-dimensional light-receiving device such as charge-coupled devices for receiving dispersed light from the grating at light-receiving positions which are two-dimensionally distributed parallel to and perpendicular to the separation flow route, and a data processor for receiving measured values obtained repeatedly by said two-dimensional light-receiving means and carrying out multi-point averaging on the measured values for each of the light-receiving positions. When a sample injected into the microchip is separated inside the separation flow route, the process of electrophoresis by this device is stopped, and light having a continuous spectrum is made incident on a specified portion of the separation flow route if the sample is to be analyzed by light absorbance. If the measurement is by fluorescence, an excitation light source will be used. If the measurement is by chemical light emission, there is no need for a light source.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIGS. 1A, 1B and 1C, together referred to as FIG. 1, show an example of a microchip which may be used as a part of the device embodying this invention, FIGS. 1A and 1B being plan views of its base plates and FIG. 1C being its side view with the two base plates joined one on top of the other;

FIG. 2 is a schematic structural diagram of a prior art device for electrophoresis;

FIG. 3 is a schematic structural diagram of a device for electrophoresis embodying this invention; and FIG. 4 is a flow chart for the operation of the device of FIG. 3.

DETAILED DESCRIPTION OF THE INVENTION

The invention is described next by way of a microchip device for electrophoresis embodying this invention shown in FIG. 3 which may be used, for example, for measuring light absorbance. Numeral 31 indicates a light source 31, such as a deuterium lamp or a xenon lamp, capable of outputting a continuous beam of light. Disposed on the optical path of the light emitted from this light source 31 is an aspherical lens 33 adapted to produce a parallel beam out of the light in the longitudinal direction of the separation flow route 5 of the microchip 1 and to converge it in the transverse direction of the separation flow route 5. Slits (not shown) are provided on both the top and back surfaces of the microchip 1, opening along the separation flow route 5. A high voltage power source 25 is connected to the microchip 1 for applying a migration potential along the separation flow route 5.

Disposed on the optical path between the light source 31 and the aspherical lens 22 is a shutter 35 for allowing or not allowing the light from the source 31 to reach the aspherical lens 33. Disposed on the side of the microchip 1 opposite from the aspherical lens 33 is a cylindrical lens 37 which is oriented such that the light from the separation flow route 5 will become parallel also in the direction of the width of the separation flow route 5. The parallel light beam from the cylindrical lens 37 is dispersed by means of a grating 39.

Disposed on the optical path of the light dispersed by the grating 39 is another cylindrical lens 41. Disposed on the side of this second cylindrical lens 41 opposite from the grating 39 are charge-coupled devices (CCD) 43 for detecting the dispersed light at each of two-dimensionally arranged light-receiving positions (x,y) according to the position x along the separation flow route 5 and the direction y perpendicular to it along which the light is dispersed according to the wavelength $\lambda$.

Connected to the CCD 43 is a data processor 47 which serves to receive detection signals from each of the light-receiving positions (x,y) of the CCD 43 through an analog-to-digital converter (A/D) 45 and to carry out multi-point averaging on a plurality of measured data for each light-receiving position (x,y).

FIG. 4 is a flow chart of the operation of this microchip device. The steps of the operations will be explained next with reference to FIGS. 1, 3 and 4.

To start, the light source 31 is switched on (Step S1) and then the shutter 35 is closed. Under this condition with no light entering from the exterior, the outputs from the light-receiving positions (x,y) of the CCD 43 are stored in the data processor 47 as the dark output D(x,y) (Step S2). The microchip 1 is thereafter set to the device (Step S3) and a migration liquid is supplied to the flow routes 3 and 5. The shutter 35 is opened for a specified length of time, and the outputs from the light-receiving positions (x,y) of the CCD 32 are stored in the data processor 47 as the background output R(x,y) (Step S4).

Next, a sample is injected into a reservoir 7 at one end of the sample introducing flow route 3, and a potential difference from the high voltage power source 25 is applied to the flow routes 3 and 5, moving the sample to the intersection area 9 of the flow routes 3 and 5. Thereafter, the potential difference applied to the flow routes 3 and 5 are changed such that the sample is introduced into the separation flow route 5 where it is separated (Step S5). After the separation of the sample is completed (YES in Step S6), the application of the potential difference is stopped, and the shutter 35 is repeatedly opened and closed at specified time intervals. When the shutter 35 is opened, the light from the source 31 converges onto a specified portion of the flow route 5 of the microchip 1 by means of the aspherical lens 33. The light which has passed through the separation flow route 5 is made parallel by the first cylindrical lens 37 and dispersed by the grating 39. Portions of this light passing through the separation flow route 5 are absorbed by the target components corresponding to their characteristic wavelengths and according to the way they are distributed through the separation flow route 5. The dispersed light from the grating 39 is individually made convergent on the CCD 43 according to the wavelength by means of the second cylindrical lens 41. The output from each of the light-receiving position (x,y) of the CCD 43 is transmitted to the data processor 47 as the target component output S(x,y) (Step S7).

Absorbance A(x,y) by a target component at position x in the separation flow route 5 and at wavelength λ corresponding to y is calculated as follows:

$$A(x,y) = -\log_{10}(\{S(xy)-D(x,y)\}/\{R(x,y)-D(x,y)\}).$$

As the measurement is repeated, the data processor 47 carries out multi-point averaging on the absorbance A(x,y) for each light-receiving position (x,y) (Steps S8 and S9) such that a detection with high sensitivity is accomplished.

If the absorbance values $A(x,y_1)$ corresponding to a particular wavelength value $\lambda_1$ are displayed continuously in the direction of positions x along the separation flow route 5, it is possible to observe the distribution of the target component along the separation flow route 5. If the absorbance values $A(x_1,y)$ corresponding to the light-receiving positions $(x_1,y)$ at a selected position $x_1$ along the separation flow route 5 are displayed continuously in the direction of wavelength λ(and hence of y), an absorption spectrum for the target component can be obtained.

The invention was described above by way of examples but these examples are not intended to limit the scope of the invention. Although a grating was shown as a means for dispersing light from the separation flow route 5, any optical means such as a prism may be substituted, as long as it is capable of dispersing the light from the separation flow route 5 for each position therealong and distributing it over a two-dimensionally arranged light-receiving positions. Although the use of a CCD was disclosed above as an example of two-dimensional light-receiving means, any two-dimensional optical sensors may be used for the purpose as long as they can obtain a spectrum corresponding to positions along the separation flow route.

Moreover, detection of a target component need not be carried out by light absorption. Target components may be detected through fluorescence or chemical light emission. If the detection is through fluorescence, the target component in the sample is marked by means of a fluorescent substance and an exciting light source is provided as the light source. A second dispersing means is further provided for leading a portion of the light corresponding to a specified wavelength from this exciting light source onto a specified range along the separation flow route. In this manner, the fluorescence spectrum can be measured at the same time. If the detection is through chemical light emission, there is no need for an optical system, the light from the separation flow route by the chemical light emission by the target component being dispersed. In this manner, the chemical light emission spectrum can be obtained at the same time.

In summary, a microchip device for electrophoresis according to this invention functions to disperse the light passing through a specified range along the separation flow route, to repeatedly measure the dispersed light by a two-dimensional light-receiving means and to carry out multi-point averaging on these measured values individually obtained for each light-receiving position. As a result, a spectrum of light from each of a plurality of positions along the separation flow route of the microchip can be obtained quickly and with high accuracy.

What is claimed is:

1. A microchip device for electrophoresis comprising:

a microchip having a separation flow route formed between transparent planar members and throughholes which are formed through one of said transparent planar members at positions corresponding to end points of said separation flow route so as to reach said separation flow route;

an electrical power source for applying a migration potential difference between said end points of said separation flow route;

a dispersing means for dispersing light received from each of positions within a specified range along said separation flow route in a perpendicular direction to said separation flow route;

a two-dimensional light-receiving means for receiving dispersed light from said dispersing means at light-receiving positions which are two-dimensionally distributed parallel to and perpendicular to said separation flow route;

a data processor for receiving measured values obtained repeatedly by said two-dimensional light-receiving means and carrying out multi-point averaging on said measured values for each of said light-receiving positions; and an optical system for switching between allowing and not allowing light to be made incident on said specified range along said separation flow route, forming a parallel beam out of light which has passed through said separation flow route to be made incident onto said dispersing means, and forming a parallel beam out of dispersed light from said dispersing means in said transverse direction, said optical system including a light source, a shutter which opens and closes to switch between allowing and not allowing light from said light source to pass therethrough, an aspherical len and a cylindrical len.

2. The microchip device of claim 1 wherein said light source emits light having a continuous spectrum, and wherein said data processor analyses said sample by light absorbance.

3. The microchip device of claim 1 wherein said light source is an excitation light source, and wherein said data processor analyses said sample by fluorescence.

4. The microchip device of claim 1 wherein said microchip also has a sample inlet flow route formed between said transparent planar members transversely to and intersecting with said separation flow route, there being throughholes reaching at both ends of said sample inlet flow route for injecting a sample therethrough, said electrical power source also serving to apply said migration potential difference along said sample inlet flow route.

5. The microchip device of claim 1 wherein said dispersing means is a grating.

6. The microchip device of claim 1 wherein said two-dimensional light-receiving means comprises charge-coupled devices.

* * * * *